United States Patent [19]

Forster et al.

[11] Patent Number: 4,518,809
[45] Date of Patent: May 21, 1985

[54] PREPARATION OF PENTYL NONANOLS

[75] Inventors: Denis Forster, St. Louis; George F. Schaefer, Olivette, both of Mo.

[73] Assignee: Monsanto Company, St. Louis, Mo.

[21] Appl. No.: 499,967

[22] Filed: Jun. 1, 1983

Related U.S. Application Data

[63] Continuation-in-part of Ser. No. 272,587, Jun. 11, 1981, Pat. No. 4,426,542, which is a continuation-in-part of Ser. No. 256,439, Apr. 22, 1981, abandoned, which is a continuation of Ser. No. 104,517, Dec. 17, 1979, abandoned.

[51] Int. Cl.³ .......................................... C07C 31/125
[52] U.S. Cl. ................................... 568/840; 568/883
[58] Field of Search ............... 568/882, 883, 840, 880, 568/845, 454, 909

[56] References Cited

U.S. PATENT DOCUMENTS

| | | | |
|---|---|---|---|
| 2,655,525 | 10/1953 | Banes et al. | 252/550 |
| 2,793,236 | 5/1957 | Habeshaw et al. | 568/883 |
| 2,844,534 | 7/1958 | Cottle et al. | 568/840 |
| 2,852,563 | 8/1958 | Hagemeyer et al. | 560/601 |
| 2,854,475 | 8/1958 | Hoog et al. | 568/882 |
| 2,921,089 | 1/1960 | Hagemeyer et al. | 560/76 |
| 2,934,568 | 4/1960 | Barker | 252/DIG. 1 |
| 3,118,954 | 1/1964 | Robbin et al. | 568/883 |
| 3,119,876 | 1/1964 | Jaros et al. | 568/451 |
| 3,127,451 | 3/1964 | Berkeley et al. | 568/882 |
| 3,401,206 | 9/1968 | Wulf et al. | 570/230 |
| 3,674,846 | 7/1972 | Brendel | 568/840 |
| 3,763,247 | 10/1973 | Lemeke et al. | 568/882 |
| 3,821,311 | 7/1974 | Hughes | 568/454 |
| 4,032,578 | 6/1977 | Savin | 568/883 |
| 4,426,542 | 1/1984 | Barker et al. | 568/883 |

FOREIGN PATENT DOCUMENTS

| | | | |
|---|---|---|---|
| 0052999 | 6/1982 | European Pat. Off. | 568/883 |
| 663240 | 12/1951 | United Kingdom | 568/840 |
| 881979 | 11/1961 | United Kingdom | 568/883 |

OTHER PUBLICATIONS

Wagner–Zook, "Synthetic Organic Chemistry" (1965) pp. 149–152 and 174–176.

Primary Examiner—Werren B. Lone
Attorney, Agent, or Firm—Joseph D. Kennedy; James W. Williams, Jr.

[57] ABSTRACT

A novel, liquid mixture of $C_{14}$ isomeric alcohols is described which is suitable for use in forming effective and biodegradable detergents, the alcohols being characterized by a 5-carbon branch at the 2-position and moderate additional branching in most isomers; the alcohols are prepared by a novel economic route from propylene dimer, involving oxo, aldol and hydrogenation reactions with the oxo reaction conducted in such a way as to give a high percentage of aldolable product and preferably with a base-catalyzed aldol reaction conducted under particular conditions to make high conversions attainable.

17 Claims, 2 Drawing Figures

PREPARATION OF PENTYL NONANOLS

This application is a continuation-in-part of Ser. No. 272,587, filed June 11, 1981, now U.S. Pat. No. 4,426,542 which is a continuation-in-part of application Ser. No. 256,439, now abandoned, filed Apr. 22, 1981 as a continuation of Ser. No. 104,517, filed Dec. 17, 1979, now abandoned.

The present invention is concerned with a process for preparing detergent hydrophobes from olefin feedstock, and with novel detergent range alcohol hydrophobes.

BACKGROUND OF THE INVENTION

The principal commercial surfactants in use today are linear alkylbenzene sulfonates and linear alcohol ethoxylates. The hydrophobic portion of both surfactants is a linear alkyl chain of between eleven and eighteen carbon atoms. These surfactants had been preceded by synthetic detergents which contain highly branched groups as a hydrophobic portion. The change to the currently employed linear groups, which occurred in the 1960's, was prompted by concern over the slow biodegradation characteristics of the branched hydrophobes. The perceived need for linearity led to development of particular approaches to hydrophobe preparation. The linear alkyl benzene sulfonates are based upon linear olefins derived from paraffins, which in turn are obtained through molecular sieve separations from paraffin mixtures. The linear alcohol based detergents are produced by way of ethylene oligomerization, followed by processes to manipulate the broad range of olefins obtained into the desired molecular weight range. The processing involved in such approaches adds considerably to energy and facilities usage and consequently to product cost. When olefins of the requisite carbon atom number have been obtained, they can be hydroformylated to produce aldehydes, generally with one more carbon atom than the olefin, which can be hydrogenated to an alcohol.

An alternate method for generating longer chain alcohols from short chain olefins is via a sequence involving hydroformylation (or oxo reaction) followed by aldol condensation and hydrogenation. Thus 2-ethyl hexanol is prepared on a very large scale by (a) hydroformylating propylene to a mixture of n-butanal and isobutanal, (b) separating the mixtures of aldehydes (c) aldol reaction of n-butanal to 2-ethylhexenal and (d) hydrogenation of 2-ethylhexenal to 2-ethylhexanol. While this approach is well-recognized to be cost effective for generation of medium chain alcohols, it has not heretofore been shown to be an economical method for generation of longer chain alcohols. Among patents teaching conversion of aldehydes to higher aldehydes by the well known aldol reaction is U.S. Pat. No. 2,852,563.

Medium chain length olefins are usually derived from dimerization or oligomerization of ethylene or propylene. Among dimerization processes is the Dimersol ® dimerization process for dimerizing olefins using a nickel coordination complex and an aluminum alkyl as catalyst. The process can convert propylene to hexenes with selectivity in excess of 85%. The hexanes can be converted by oxo reaction to aldehydes and then alcohols, producing heptanols. Processes are also known for dimerizing propylene with trialkylalumminum metals to 4-methyl-1-pentene, see Industrial Organic Chemistry, Klaus Weissermel and Hans-Jurgen Arpe; English translation by Alexander Muller (Verlag Chemie, Weinheim, New York, 1978), pp 75–77. Also oxo reactions of certain branched olefins have been studied, see M. Johnson, Chem. Soc. 1963, 4859; Piacenti et al, J. Chem. Soc., 1966, 488; and Vysokinskii et al, J. Applied Chemistry of USSR, 1972, Vol. 45, pp. 1352–1355. Also oxo reactions of certain non-terminal octenes have been reported to give less than 60% of the straight chain aldehyde isomers, see Kummer et al, Homogeneous Catalysis-II, pages 19 to 26, Advances in Chemistry Series 132 (Edited by Denis Forster and James F. Roth), American Chemical Society, Washington D.C., 1974.

Reactions of the type described characteristically produce mixtures of products, often with extensive branching. Therefore, in order to control the branching, or to eliminate unreactive components, it has been common practice to employ distillation at intermediate stages to remove some of the isomer.

SUMMARY OF THE INVENTION

The present invention concerns a hydrophobe alcohol mixture composed almost entirely of $C_{14}$ alcohols with a structure branched at the 2-position, being generally 2-pentylnonanols, i.e. having a five-carbon alkyl group substituted on the 2-position of a nine-carbon alkanol; with most of the isomers in the mixture having moderate additional branching, primarily methyl groups. The mixture is liquid at ambient temperatures and the hydrophobe groups of the alcohols are such as to make the mixture useful for formation of very effective detergents. The alcohol structures are further characterized by the absence of quaternary carbon or other structures strongly resistant to biodegradation, while generally having vicinal branching within limited ranges, and are still suitably biodegradable.

The invention is further directed to processes for converting olefins to described $C_{14}$ alcohols, involving dimerization, oxo, aldol and hydrogenation processes based on propylene. In particular, a process involves conducting an oxo reaction with a hexane mixture comprised mainly of methyl pentenes, as produced by dimerization of propylene, and obtaining a heptanal product in which carbonylation has occurred primarily on terminal carbon so that upwards of 75% of the heptanal isomers are unbranched at the 2-position and capable of reacting directly in aldol reactions under basic conditions; and conducting an aldol reaction of the heptanal product to obtain $C_{14}$ aldehydes which are then hydrogenated to $C_{14}$ alcohols. the invention further includes use of cobalt catalyst in the oxo procedure under conditions to produce high percentages of desired aldolable product, and utilization of a co-solvent and suitable aldol conditions to obtain the $C_{14}$ product. Fortuitously, it has been found that in the hydroformylation of isomeric hexenes, the formylation of the prominent 2-methyl-2-pentene isomer occurs primarily on a terminal bond, with the percentage of such terminal formylation being much higher than that generally characteristic of hydroformylation of internal olefins; and a high percentage of aldolable product is obtained from terminal formylation of isomeric hexenes. The present invention involves an efficient process for converting propylene dimers to detergent hydrophobe alcohols in high overall yields such as 70% or better, and the alcohols are suitable for conversion to detergents having detergent and biodegradation properties comparable to those of the common commercial detergents. Moreover, the present process provides a much more efficient and economical route to detergent hydrophobes from olefin feedstock than that provided by the routes prominent in present commercial use. This route permits detergent alcohols to be built up from low cost propylene as compared to present commercial processes based on ethylene.

DETAILED DESCRIPTION OF THE INVENTION

Figure 1:
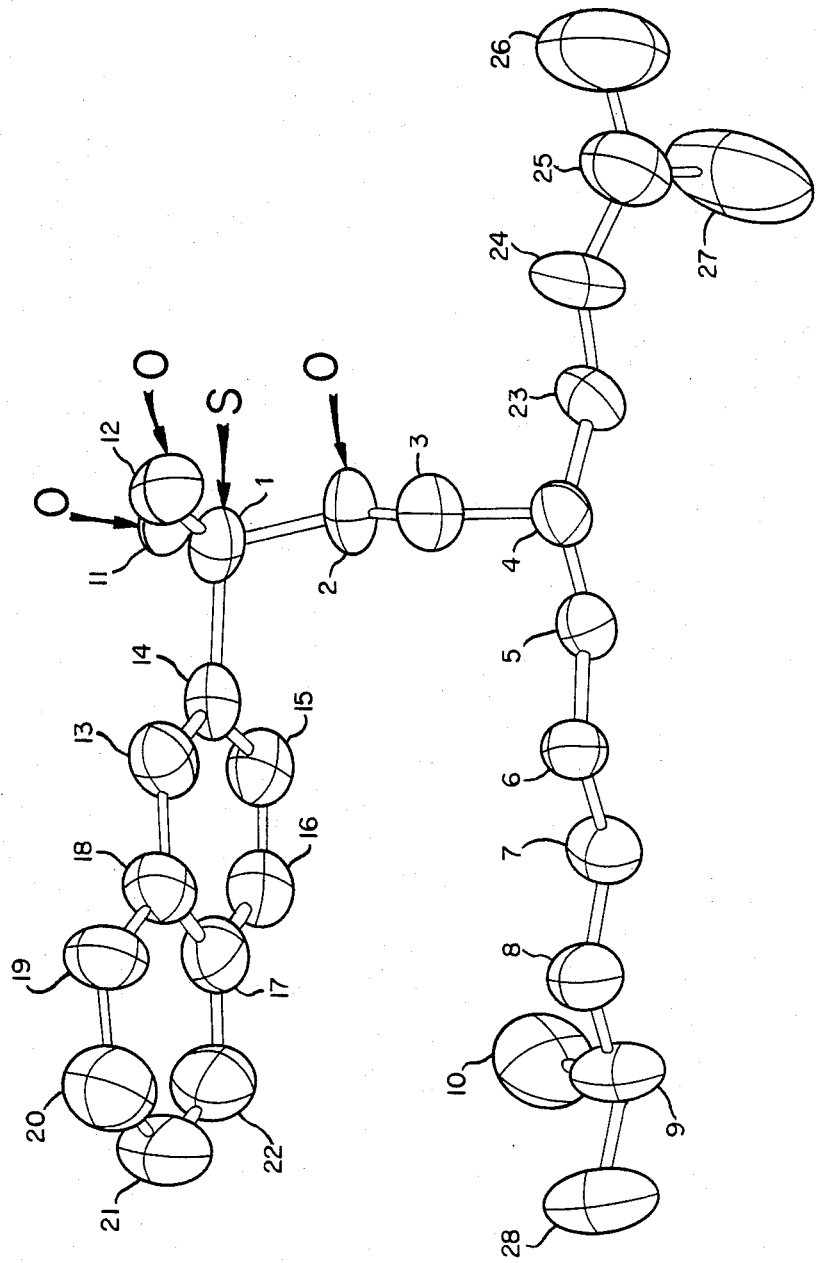

The alcohols of the present invention can be represented:

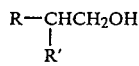

in which R is an alkyl group with seven carbon atoms and R' is an alkyl group with five carbon atoms. In a high percentage of the alcohols in the mixture, generally more than 80–85% or so, R' is selected from n-pentyl, 3-methylbutyl and 1-methylbutyl, and R is selected from n-heptyl, 3-methylhexyl, 5-methylhexyl, 2-methylhexyl and 2-ethylpentyl groups. While there will be some variance in the alcohol mixture with variation in preparation conditions, generally close to 50% or so of the alcohol mixture will be composed of 2-(3-methylbutyl)-5-methyl-octanol,2-(1-methylbutyl)5-methyloctanol and 2-pentyl-5-methyloctanol. Considering the type of branching involved, close to 50% or so by weight of the alcohols will have branching not only at the 2-position, but with each branch having an addition methyl branch, i.e. with R' and R in the above formula being selected from methylbutyl and methylhexyl groups respectively. The alcohols are also characterized as generally having a limited amount of vicinal substitution, i.e. substitution or branching on adjacent carbon atoms, and little or virtually no di-substituted carbon chain atoms, i.e. quaternary carbon atoms. Significant amounts of alcohols with quaternary carbon atoms have not been found in product analyses, and the types of reactants and reactions used in product preparations make it very unlikely that significant amounts of such alcohols would be found in unidentified portions of products. The lack of quaternary carbon in the alcohols of the mixture is fortunate in that such carbon is ordinarily resistant to biodegradation.

With further regard to the particular $C_{14}$ alcohol mixture, approximately 40 to 60% by weight will generally be the 2(3-methylbutyl)-5-methyloctanol, 2-(1-methylbutyl)-5-methyloctanol and 2-pentyl-5-methyloctanol; and at least about 65% and possibly 65 to 80% or so by weight will be comprised of these alcohols, along with 2-(3-methylbutyl)-7-methyloctanol, 2-pentylnonanol, 2-pentyl-7-methyloctanol and 2-(3-methylbutyl)-nonanol. In addition to the indicated ranges of these alcohols, various other $C_{14}$ isomers will be present in small percentages, particularly those other alcohols listed in Table 4 herein, in amounts by weight usually approximating those in the Table and generally no more than 5% each and usually in ranges up to 1 to 2% or so, and with the balance of the $C_{14}$ alcohols being generally composed of the other alcohols in Table 3 herein, which will generally be present only in small percentages of each isomer. It will be noted that those isomers present only in small amount, with no amount reported in Table 4, but included in Table 3, tend to be more highly branched, i.e. multi-branched, than the other isomers, although most branches are still methyl, or occasionally ethyl groups. Taking these isomers into consideration, the amount of vicinal branched material may range as high as 20 to 35% or so by weight of the $C_{14}$ alcohols. However, the mixtures of alcohol isomers are biodegradable as indicated by tests reported herein. One of the alcohols which can be present in fairly good proportion, such as 10 to 20% or so, 2-(1-methyl-butyl)-5-methyloctanal is a vicinal branched alcohol. The alcohols in the mixture are characterized by a fair degree of branching, although the alcohols present in large amount tend to be less branched than some of the minor components. Thus the 18 or so alcohols constituting about 90–95% or so by weight of the alcohols have an average of slightly more than 2 branches, about 2.2 to 2.4 branches, while the other 5 to 10% of the alcohols may have upwards of above 3.5 branches, such as 3.75–3.8 branches.

In addition to the novelty of the alcohol mixtures of the present invention, the particular alcohols are also new except for the 2-pentylnonanol. Thus the other 27 alcohols named in Table 3 are new compounds suitable for formation of nonionic detergents.

The alcohols comprising most of the present alcohol mixtures can also be represented by the formula:

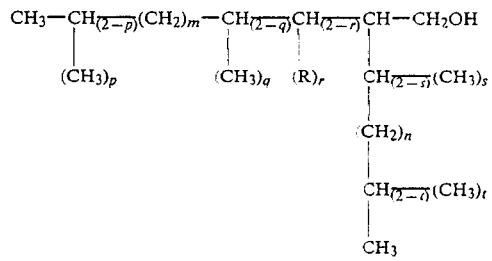

wherein:
R = methyl or ethyl;
p, q and r = 0 or 1; but only one of p, q and r can be 1;
m = 3, when p, q and r = 0;
m = 2, when p or q = 1;
m = 2, when r = 1 and R = methyl;
m = 1, when r = 1 and R = ethyl;
n = 2, when s and t = 0;
n = 1, when s or t = 1;
s and t = 0 or 1, but only one of s and t can be 1.

The alcohol mixtures, and the individual components thereof, are liquids at ambient temperatures. This is advantageous in that the alcohols can be more readily transferred from one vessel to another, or moved by pumping through conduits, etc., than is the case with solid alcohols. Also the liquid form is more convenient for mixing with reactants and solvents for conversion to detergent compounds or other useful products as contemplated. It happens that $C_{14}$ alcohols with straight chains, or with considerably less branching than the present alcohols, are generally solids. Thus detergent alcohols obtained by way of ethylene oligomerization, such as 75% to 80% normal primary $C_{12-15}$ alcohols and 75% normal $C_{14}$ primary alcohols, consisting of the designated percentages of normal alcohols and the balance of isomeric 2-alkyl(primarily 2-methyl)primary alcohols, are solid materials.

The detergent alcohols of the present invention are particularly suitable for conversion to nonionic detergents of good detersive and biodegradation properties. The largest volume use of detergent alcohols is as nonionic surfactants. The polyethoxylate surfactants are particularly important, and can be generated from the present alcohols by base catalyzed reaction between ethylene oxide and alcohol:

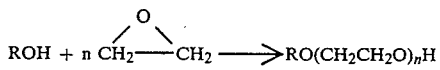

Typical values of n are in the range of 6 to 12, and R represents the alkyl portion of the alcohol, which for the present alcohols is generally a 14-carbon alkyl group. Ethoxylates prepared from the present alcohols were tested for detergency and found to be comparable to a leading commercial nonionic detergent under a variety of washing conditions. The commercial detergent is that prepared from $C_{12-15}$ alcohols of 75–80% linearity, Neodol ®25.

In addition to detersive properties, another concern with surfactants has been biodegradability. The first major synthetic detergents were so-called alkylbenzene sulfonates, with an alkyl hydrophobe group derived from propylene tetramer. The propylene tetramer was produced by acid catalyzed polymerization and hence was highly branched, including extensive quaternary branching. This gave rise to a product with rather poor biodegradation properties, which led to extended life for surfactant properties in rivers and lakes. Public concern over the asthetic impact (foam) and possible toxicity of long lasting surfactants led to a voluntary change over to predominantly linear hydrophobes. Prominent among current surfactants are linear alkylbenzene sulfonate and the linear alcohol ethoxylates discussed above. The linear alkylbenzene sulfonate (LAS) involves a linear alkyl group substituted on a benzene ring, generally at one of the secondary carbon atoms of the alkyl group. LAS has been found to be a suitably biodegradable detergent, although being degraded somewhat more slowly in standard tests than the substantially linear alcohol ethoxylates. The ethoxylates produced from the alcohols of the present invention are comparable in biodegradation to LAS, and therefore suitable in this regard. It is fortunate to find that the present alcohols are biodegradable, despite the presence of multiple branching. The substantially linear alcohol ethoxylates, such as Neodol ®25, are known to be biodegradable, but those alcohols include substantial percentages of linear alcohols, and the branching is ordinarily only a single methyl or other lower alkyl group. In contrast, most of the alcohols in the present mixture have more than two alkyl branches. It is advantageous to be able to produce the present detergent alcohols, of properties comparable to Neodol ® alcohols, in a more efficient process and from a less expensive feedstock, i.e. from propylene rather than from ethylene.

Hexenes, as produced by dimerization of propylene with transition metal catalysts, as in the Dimersol ® dimerization process, are characterized by being composed mainly of internal olefins, and a linear content which has a range from about 20% up to 32% or so. The main isomer present is a 2-methyl-2-pentene, along with other 2- and 4-methyl pentenes and around 6% 2,3-dimethyl-2-butene.

As indicated above, the linear content of propylene dimers is fairly low, being around 20% to 30% or so. At times there may be advantage in separating the linear components prior to conducting the present process. Separation can be effected by use of a molecular sieve or other suitable procedure. However, it has been found that the entire hexenes portion of the propylene dimerization product can be utilized as feedstock for the present oxo-aldol process. The branched isomers are typified by 2-methyl-2-pentene which, when subjected to oxo reaction with cobalt catalyst, has been found to be very selectively converted to 3-methyl and 5-methyl-hexanals. Fortunately it has been found that cobalt catalyst, in contrast to rhodium, has the effect of isomerizing the internal olefins so that the aldehyde group is predominantly on the end of the chain. It is very important to the use of propylene dimer in the present process, that the oxo product is predominantly a non $\alpha$-branched alkanal., i.e. there is no substituent in the 2-position. Such aldehydes, which will directly react in base-catalyzed aldol reactions are sometimes referred to herein as "aldolable" aldehydes. As discussed herein, aldehydes with substituents in the 2-position do not readily undergo base-catalyzed aldol reactions. Thus if the internal hexenes were converted largely to such unreactive aldehydes, it would be very difficult to effect self-condensation of such aldehydes to a useful extent, and the use of propylene dimers in the present oxo-aldol process would be impractical. However, as discussed herein, the oxo process with cobalt catalyst converts the hexenes largely, e.g. 75 to 80% or so, to aldehydes which will react in the aldol reaction, making hexenes, obtained from propylene dimerization very suitable as a feedstock for producing detergent range alcohols in accord with the present invention. This result is surprising in view of the fact that oxo reactions of certain non-terminal octenes are reported to give less than 60% of straight chain aldehyde isomers. It appears that the methyl substituent has some influence in directing the oxo reaction to obtain a great predominance of aldehydes with no substituent in the 2-position.

Particular branched hexene isomers are converted to non $\alpha$-branched alkanals with very high selectivity, with 2-methyl-pentene-1 selectivity of better than 90% to such aldehydes being obtainable. The mixture of both branched and linear hexenes from propylene dimerization can be converted to such aldolable aldehydes with selectivity such as about 79% or so. In contrast, the selectivity to such aldehydes from the linear hexenes may be only 60% or so. Thus, surprisingly it is found that higher selectivity to aldehydes desirable for the aldol reaction can be obtained by using the crude hexenes mixture for the oxo reaction, rather than only the linear hexenes. Depending upon relative value and availability of the linear and branched hexenes, one might find advantage in using only the branched hexenes in the present process because of the high selectivity in the oxo process to aldehydes with no 2-branching suitable for aldol reaction.

The present invention employs an oxo reaction of substantially branched hexenes to obtain a mixture of aldehydes, which is then subjected to an aldol reaction. The oxo reaction involves contacting hexenes with hydrogen and carbon monoxide and hydroformylation catalyst under hydroformylation conditions suited to obtaining a high proportion of terminal formylation of the olefin feed. It is desirable to have the resulting aldehyde constitute 75 to 80% or more of the aldehyde product.

It is important that the hydroformylation of the mixed hexenes give a relatively high ratio of aldehydes without 2-branching, as this contributes to the feasibility of using the aldehyde mixture for an aldol reaction to obtain a good yield of aldol product. The use of moderate temperatures in the hydroformylation contributes to forming aldehydes without 2-branching, but reaction rate improves with temperature. Thus temperatures sufficient to produce an appreciable reaction rate, ranging from 80° to 100° C. or so can be used, and temperatures on up to 125°-140° C. can be employed to obtain better reaction rates. Still higher temperatures up to 150° C. or higher can be used. To some extent high catalyst concentrations can be employed to obtain reaction rates, even at relatively low temperatures. Cobalt catalyst is especially suited to obtain the desired high proportion of aldehyde with no 2-branches. Unmodified cobalt carbonyl catalyst can conveniently be used. Such catalyst conventionally designated as cobalt octacarbonyl, can be provided or employed in many forms known to be useful as a hydroformylation catalyst, although it may be necessary to exercise some choice to provide catalyst best suited to obtaining a high proportion of aldehyde with product suitable for direct base-catalyzed aldol reaction.

The oxo stage of the reaction can be conducted under the usual conditions pertaining to cobalt catalyzed hydroformylation reactions with attention to the temperature conditions as described above. Usual pressure conditions apply, such as 500–4000 or up to 5000 psi (3447.5–27,580 on up to 34,475 kilopascals) total pressure, with most of the pressure being from the carbon monoxide and hydrogen supplied. The carbon monoxide and hydrogen are conveniently used in 1:1 ratio and obtained from usual synthesis gas sources, but other ratios can be employed in keeping with known hydroformylation practice. The reaction can be carried to the desired stage of completion in 1 to 3 hours or so on a batch basis, varying with time, temperature, pressure and catalyst concentration.

The reaction can be conveniently conducted either without a solvent or with solvents and, employing concentrations customary for homogeneous catalyst reactions, such as 2 to 10 molar or greater concentrations of the hexenes in a solvent, e.g. hydrocarbon solvents such as toluene, and 0.1% to 1% by weight, based on cobalt, of catalyst.

The aldol reaction is carried out for the most part utilizing the usual aldol catalysts and temperature conditions, using elevated temperatures upwards of 60° C., particularly temperatures of about 90° C. to 130° C., or possibly up to 150° C. or higher if desired. The reaction is operable over broad pressure ranges including pressures less than atmospheric as well as elevated pressures, but will usually be effected at slightly elevated pressures sufficient to maintain the reactants substantially in the liquid state. The reaction can also conveniently be conducted at reflux.

The aldol reaction can utilize strongly alkaline catalyst, such as sodium and potassium hydroxide, or sodium and potassium cyanide. The concentration of the aqueous alkali can be varied, but molar or similar concentrations of alkali metal hydroxides can be used, and concentrations selected will generally be in the range of about 1 to 10% by weight. The amount of aqueous alkali to aldehyde reactant can also vary, for example from about 15% by volume aqueous alkali up to about 75% by volume aqueous alkali. The aldol reaction will be run for a sufficient time to obtain the desired degree of conversion, which for batch reactions may be in the range of about 1 to about 3 hours, while in continuous reaction times of less than five minutes are achievable. The reaction is stopped by permitting the reaction mixture to cool and separating the organic reaction phase from the aqueous alkali phase.

In one major respect it is difficult to conduct aldol reactions of heptanals in conventional manner, as in aqueous NaOH, because this procedure requires appreciable solubility of the organic aldehyde in the aqueous phase, or vice versa. The mutual solubility is so low with $C_7$ aldehydes that little reaction occurs in reasonable time periods. However, it has been found that use of a co-solvent overcomes this problem and results in suitable reaction rates. In principle, any solvent with miscibility with both the aldehyde and the aqueous base, or at least some solubility with respect to each, will act to increase the rate of the reaction. It is also desirable that the solvent be relatively inert under the reaction conditions so as not to cause interfering reactions or to be readily degraded excessively by the hot basic medium. In general, polar solvents will tend to have the requisite solubility characteristics, and hydroxy alkanes, for example, alkane diols, having the appropriate solubility characteristics can be used. Hexane diol is very suitable. Methanol is also a suitable cosolvent.

In the aldol reactions involved in the present invention it is necessary to utilize a high proportion of aldehydes without 2-branching, also referred to herein as aldolable aldehydes, in order to achieve good yields of aldol. The 2-substituted aldehydes do not undergo self-condensation aldol reactions with any facility under the usual basic aldol conditions, although they will seve as acceptor molecules to some extent in cross-aldol reactions, as illustrated with the following heptanal isomers:

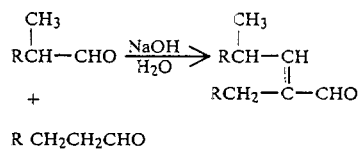

in which R represents a butyl group. However, the 2-substituted aldehydes react more slowly than other aldehydes, and therefore would constitute an undesirably high residue of unreacted component if provided to the reaction mixture in which proportion. In the present process with 75 to 80% or so of aldehydes without 2-branching, the aldol reaction can be conducted to include some cross-aldol of 2-substituted aldehydes so as to have yields of 85% or more based on starting aldehyde. In general, the $C_{14}$ aldehydes resulting from such cross-aldol reactions, and the alcohols produced therefrom, have properties comparable to those produced from aldol reactions of aldehydes without 2-substitution, and are suitably present in alcohol mixtures for detergent preparations as described herein. The conversion of aldehydes without 2-branching in such aldol reactions can be in the range of 95% or better while possibly only about ¼ to ⅓ of the 2-substituted aldehydes are converted to aldol product.

The hydrogenation of the enals from the aldol reaction can be conducted under the usual catalytic hydrogenation conditions for reducing olefinic bonds and aldehyde groups. The carbon-to-carbon bond reduces more rapidly and at a lower temperature than the aldehyde group, e.g. at about 90° C., with cobalt on Kieselguhr catalyst at elevated hydrogen pressure. The hydrogenation will generally be carried out at 100–20000 psi, or greater hydrogen pressures and temperatures of 100° to 200° C. or higher, although any temperatures which are effective with a particular catalyst can be used. The stated conditions will be effective for reducing both the carbon-to-carbon bond and the aldehyde group to obtain saturated alcohol. Various other hydrogenation catalysts can be used including platinum and platinum on carbon catalysts, copper chromite, activated nickel, etc., and individual catalysts can be utilized in conjunction with other catalysts.

The present invention involves an oxo reaction, followed by an aldol reaction, and then a hydrogenation to convert enals to alcohols. For large scale operations, the oxo reaction will be conducted with usual provisions for separating gaseous reactants and products, and catalysts, from the aldehyde prducts, with recycle as appropriate. The aldehyde product mixture will then be subjected to an aldol reaction, followed by decantation and water washing or other simple procedures to separate the organic product-containing phase from the aqueous phase. The product phase is then hydrogenated, converting both unreacted heptanals and $C_{14}$ enals to the corresponding alcohols. The hydrogenation is followed by a distillation to remove light ends, followed by a distillation to remove $C_7$ alcohols. Both the $C_7$ and $C_{14}$ alcohols can then be treated in further hydrogenation polishing operations to improve the alcohol quality by insuring complete hydrogenation.

The separation of the $C_7$ from $C_{14}$ alcohols is readily effected by distillation in equipment constructed of inexpensive alloys such as carbon steel. Separation at this stage is simple, compared to the difficult separation which would be required to separate the seven carbon aldehyde isomers prior to the aldol reaction.

As an alternate to the above procedure, it is possible to separate the unreacted seven-carbon aldehydes by distillation from the 14 carbon enals prior to hydrogenation. For convenience of separation, distillation of the alcohols is generally preferred, and then the seven-carbon components are in the form of alcohols. However, if the aldehydes are desired for some purpose, separation is appropriate, and this has the advantage of avoiding unnecessary hydrogen use.

In the present process the oxo product is used in the aldol reaction without any need for separation of some of the components. This contrasts with the usual commercial procedure, for example, for preparing 2-ethylhexanol as a plasticizer alcohol, wherein it is the practice to remove isobutanal before conducting an aldol reaction with n-butanal. The separation is effected by distillation and, since isomeric aldehydes have similar boiling points, separation on a commercial scale involves high capital cost equipment with consequent expense, and a substantial energy cost. There is a definite advantage in avoiding such a distillation step in the present process.

The $C_7$ branched aldehydes which do not react in the aldol reaction can be separated from the reaction mixture for various purposes, or hydrogenated with the mixture and utilized as a $C_7$ branched alcohol. If desired, the branched $C_7$ alcohol can be dehydrated, and then subjected to an oxo reaction to produce an aldehyde with an additional carbon atom. Thus 2-methylhexanol can be converted to 2-methylhexene-1, which can be recycled to the oxo stage of the reaction process and hydroformylated to predominantly 3-methyl-heptanal. This 3-methylheptanal, not having any substituent in the 2-position, reacts at a good rate in the aldol reaction. Other unreacted aldehydes, such as 2,4-dimethylpentanal and 2-ethyl-pentanal, can similarly be hydrogenated and dehydrated and recycled to be converted in the oxo stage to $C_8$ aldehydes with no substituent in the 2-position, which will take part in the aldol reaction when recycled through that stage. This procedure to use the unreacted $C_7$ aldehyde results in greater conversion of the original reactants to the desired final product, rather than to a concomitant product such as $C_7$ alcohols. Use of this recycle feature in the oxo-aldol process changes the components of the product from mixed hexenes to some extent, but the properties will be similar as the main difference in the additional components will be an additional methyl substituent as in 2(1-methylbutyl)-5-methylnonanol, 2-(3-methylbuty)-5-methylnonanol and 2-pentyl-5-methylnonanol, for example.

The Dimersol ® dimerization process has been referred to in various publications, e.g. see "How First Dimersol is Working" by Benedek et al, Hydrocarbon Processing, May 1980, page 143; also Chauvin et al, "The IFP Dimersol ® Process for the Dimerization of $C_3$ and $C_4$ Olefinic Cuts", Advances in Petrochemical Technology, presented at American Institute of Chemical Engineers, Apr. 13, 1976, Kansas City, Mo.

The combination of the Dimersol ® dimerization process, oxo process, aldol and hydrogenation provides a very efficient route from propylene to detergent range alcohols. One of the known routes to such alcohols relies upon oligomerization of ethylene to obtain higher molecular weight materials which are then subjected to an oxo reaction. The presently proposed route is in many respects more efficient and economical than those involving ethylene oligomerization, as propylene costs less than ethylene, and the reactions involved using dimerization, oxo and aldol are more straight forward than an oligomerization which can produce a broad mixture of products and require extensive equipment and procedures to direct it to suitable product. As discussed hereinabove, the mixture of isomers obtained from a dimerization can be carried through the oxo, aldol and hydrogenation reactions to obtain high overall conversions and yields, despite the presence of extensive branching in the materials. It is fortunate to find that a high proportion of the materials are capable of taking part sequentially in all of the required reactions, and in particular that the aldehyde failing to react to a significant degree in the aldol reaction, because of 2-substitution, is at a comparatively low level.

In the oxo stage of the present process it will be noted that cobalt catalyst is employed with the hexenes in order to promote migration of the olefinic bond and high selectivity to desired aldehyde isomers, such catalysts being for example $Co_2(CO)_8$ which may be equivalent to $HCo(CO)_4$ under reaction conditions.

The $C_{14}$ or other detergent range alcohols produced by the present process can be readily converted to detergents by known procedures. Thus non-ionic detergents are prepared by reaction with ethylene oxide to have a desired number of ethoxyl groups, e.g. 6 to 10 or 12 or so. These, or other ethoxylated alcohols, possibly with 2 to 3 ethoxyl groups can be reacted to form an alcohol ether sulfate, having a sulfate anionic end group with a sodium or other cation. The alcohols can also be reacted to prepared sulfate derivatives. The detergents thus prepared will have the requisite hydrophobic groups for detergent properties. Moreover, the structures are such as to provide biodegradability, in that the structures are acyclic alkyl groups which are essentially free of any quaternary carbon groups. There is some branching on adjacent carbon atoms, but that and the common 2-branching characteristic of aldol product, with or without various additional methyl or other lower alkyl branches in non-adjacent positions, do not have any important effect on the biodegradable nature of the compounds. An alcohol ether sulfate prepared from 2-pentylnonanol has been described as biodegradable by Crawland et al, Surfactant Congress No. 4, Vol. 1, page 93 (1967). Also Kravetz et al, Proceedings of the American Oil Chemists' Society, 69th annual meeting, May, 1978, St. Louis, MO., concluded that variation of branching from 45% to 75% linear had no appreciable effect on biodegradation rates of primary alcohol ethoxylates, and make reference to 58% branching giving biodegradation at rates not appreciably different from zero branching. The branching involved there was a single branch, primarily a methyl group, but with some proportion of other lower alkyl groups.

A quantity of Dimate ® hexenes from a refinery stream was distilled to have a $C_6$ cut, approximately 73% of the total material. Analysis is given in Table 1. The Dimate ® hexenes had been produced by dimerization of propylene over a catalyst by the Dimersol ® process.

TABLE 1

Dimersol ® Hexene Distribution

|  | % (100% basis) |  |
|---|---|---|
| 2,3-dimethyl-2-butene | 4.5 |  |
| 2-methyl-2-pentene | 35.6 |  |
| trans-4-methyl-2-pentene | 18.4 |  |
| cis-4-methyl-2-pentene | 3.7 |  |
| 2-methyl-1-pentene | 5.1 |  |
| 2,3-dimethyl-1-butene + 4-methyl-pentene | 1.7 |  |
| trans-2-hexene | 17.8 |  |
| trans-3-hexene | 6.3 | 31.0 linear |
| cis-3 + cis-2 hexene | 6.8 |  |
| 1-hexene | 0.1 |  |

The distillation serves to remove some $C_5$, $C_7$ and $C_9$ hydrocarbons resulting from oligomerization involving some ethylene present in the original olefin feed, or trimerizations. It also removes $C_6$ chlorides, along with the $C_9$ hydrocarbons; these chlorides, resulting from the dimerization catalyst, could contaminate the oxo catalyst if not removed.

It is fortunate that the hexenes mixture is amenable to reaction at a good rate in the oxo reaction. It is sufficiently reactive to permit use of moderate conditions and equipment thereof, with suitable reaction rates and times. This is in contrast to an octenes Dimate ® mixture which is characterized by more relatively unreactive dibranched olefin isomers and much slower reaction rates. Such material requires more severe reaction conditions in more expensive equipment, and additional reactor capacity.

Since the oxo product is to be reacted in an aldol reaction, it is to be conducted under conditions which favor production of aldehydes as contrasted with alcohol or other products. Consequently, phosphine-modified or similar cobalt catalysts should be avoided as they tend to cause hydrogenation of the aldehyde intermediate to an alcohol.

EXAMPLE 1

Hydroformylation of a Dimate hexenes mixture, of composition reported in Table 1, was carried out in an autoclave with agitation. The autoclave was charged with 0.52 g dicobalt octacarbonyl, 74.06 Dimate hexenes and 3000 psi. gauge (20,786 KPa) of 1:1 CO and $H_2$. The autoclave was heated to 130° C. and held for four hours. Liquid samples were taken every hour. The autoclave was cooled rapidly and the product removed under nitrogen. Analysis indicated 92% conversion of the olefins. The product was analyzed chromatographically, with results as reported in Table 2 (along with other examples). It will be noted that 77.9% of the aldehyde product was unbranched at the 2-position and therefore aldolable. This result was obtained, even though the hexene reactants were more than 90% composed of internal olefins, including some linear hexenes which give product little more than 50% aldolable. A similar run employing a 110° C. temperature with cobalt catalyst for 23 hours is also reported.

EXAMPLE 2

The autoclave of Example 1 was charged with 0.49 g. of dicobalt octacarbonyl, 69.84 g. 2-methylpentene-2 and 3000 psi gauge (20,786 KPa) of CO and $H_2$ in 1 to 1 ratio. The autoclave was heated to 130° C. and held at this temperature for three hours. The autoclave was cooled and the product removed under a blanket or argon, and analyzed. Conversion of the olefin was 83%. The procedure was repeated substantially, but employing a temperature of 116° C. for a 48% conversion. Results of the analysis are reported in Table 2. It is notable that better than 90% of aldehydes unbranched at the 2-position, i.e. aldolable aldehydes, were obtained. Approximately the same results were shown from samples taken during the reactions, with the 116° reaction at 1 hour giving 17% conversion and 35.4% 5-methylhexanal and 55.5% 3-methylhexanal; and the 130° reaction temperature 45% conversion at 1 hour with 32.5% 5-methylhexanal and 57.6% 3-methylhexanal.

EXAMPLE 3

Hydroformylation was carried out on 2-methyl-1-pentene with cobalt catalyst in accord with the procedure of Example 2 at 116° C. for a three-hour period. A 41% conversion was obtained, with 95% of aldolable aldehyde unbranched at the 2-position being obtained. Results are reported in Table 2.

EXAMPLE 4

Hydroformylation was effected with 4-methyl-2-pentene in accord with the Example 2 procedure, employing a 130° C. temperature. Results are reported in Table 2.

TABLE 2

| | | | | | Oxo Product Distribution % | | | | | | | | |
|---|---|---|---|---|---|---|---|---|---|---|---|---|---|
| Example | Hexene | Temp. (°C.) | Run Time (hours) | I | II | III | IV | V | VI | VII | VIII | IX | % Aldolable* |
| 1 | D-Mixture | 110 | 23 | 15.3 | 19.4 | 8.7 | 39.1 | 4.4 | 3.1 | 1.4 | 7.5 | 1.0 | 76.9 |
| " | D-Mixture | 130 | 4 | 14.9 | 25.0 | 8.5 | 36.2 | 4.3 | 1.8 | 1.1 | 7.4 | 0.8 | 77.9 |
| " | " | | 3 | 15.4 | 23.5 | 8.8 | 37.9 | 4.5 | 0.7 | 1.1 | 7.5 | 0.7 | 77.5 |
| " | " | | 2 | 16.8 | 25.5 | 9.6 | 33.8 | 4.9 | 0.8 | 1.0 | 7.2 | 0.6 | 76.9 |
| " | " | | 1 | 18.8 | 24.5 | 10.7 | 31.8 | 5.4 | trace | 1.4 | 6.8 | 0.5 | 75.1 |
| 2 | 2-methyl-2-pentene | 116 | 3 | — | 34.3 | — | 56.6 | — | — | 1.3 | 6.9 | 0.9 | 90.9 |
| " | 2-methyl-2-pentene | 130 | 3 | — | 33.6 | — | 56.6 | — | — | 1.4 | 7.2 | 1.2 | 90.2 |
| 3 | 2-methyl-1-pentene | 116 | 3 | — | 10.6 | — | 84.4 | — | — | 0.4 | 2.5 | 2.1 | 95.0 |
| 4 | 4-methyl-2-pentene | 130 | 3 | | 65.9 | | 17.3 | | trace | 1.6 | 15.3 | trace | 83.2 |
| | | | 2 | | 65.1 | | 16.6 | | | 1.6 | 16.8 | trace | 81.7 |
| | | | 1 | | 67.6 | | 14.2 | | | 1.4 | 16.8 | trace | 81.8 |

I = heptanal
II = 5-methylhexanal
III = 2-methylhexanal
IV = 3-methylhexanal
V = 2-ethylpentanal
VI = 3,4-dimethylpentanal
VII = 2,-ethyl-3-methylbutanal
VIII = 2,4-dimethylpentanal
IX = 2,2-dimethylpentanal

EXAMPLE 5

Hydroformylation was effected with 2,3-dimethyl-2-butene at 130° C., employing the procedure of Example 2. At 1, 2 and 3 hours conversions were respectively 18, 43 and 71%, and in each case the aldehyde product was analyzed as 100% 3,4-dimethylpentanal, an aldolable aldehyde.

EXAMPLE 6

This example was a simulation of two oxo reactors operating at different temperatures. The autoclave was charged with 0.44 g. dicobalt octacarbonyl, and 73.94 g. Dimate hexenes. The autoclave was sealed, pressure checked and run under 3000 psig (20,786 KPa) of 1/1 CO to $H_2$ at 130° C. for 1 hour then heated to 140° C. for an additional 4 hours. The autoclave and contents were rapidly cooled and the product removed under nitrogen. Analysis of the final product yielded that the olefin was 97% converted with 83% as the aldehydes, 11% as alcohols, and 3% high boilers. The unreacted olefin consists of 2-methylpentene-2, 2,3-dimethylbutene-2 and trans-hexene-2. The aldehydes after normalization are 39% 3-methylhexanal, 20% 5-methylhexanal, 16% heptanal, 9% 2-methylhexanal, 6% 2,4-dimethylpentanal, 5% 2-ethylpentanal, 4% 3,4-dimethylpentanal, 1% 2-ethyl-3-methylbutanal, 1% 2,2-dimethylpentanal. The aldehydes were distilled from the catalyst, unreacted starting material and other products at 20 mmHg from 41° to 45° C.

The percentage of aldehydes unbranched at the 2-position produced was 79%.

The results in Example 6 indicate that the percentage of aldehydes unbranched at the 2-position from branched hexenes (69% of hexenes) was 88.7%, compared to only 53.3% of such aldehydes from the linear hexenes (31% of hexenes). Considering only the methylpentenes (62.8%, ignoring the small amount with 2,4-dimethylbutene in Table 1), the aldolable aldehyde unbranched at the 2-position content of the aldehyde product was 86.6%).

EXAMPLE 7

An aldehyde mixture representative of that from the oxo reaction of Dimate ® hexenes, as described in Example 16, was reacted in an aldol reaction. An autoclave was charged with 50 ml of 0.8M NaOH, 100 ml of 2,5-hexanediol under 20 psi gauge argon. Then 36.2 g., 50 ml, of the aldehydes were pressured into the autoclave with argon after the autoclave had been heated to 100° C. and agitation set at 1500 rpm. The reaction was run for an additional hour and the system rapidly cooled. The product was removed and the upper and lower phases were separated. The upper phase contained 16.8% unreacted aldehydes, 2.4% heptanols, 72.9% tetradecenals and 4.1% 2,5-hexanediol. The conversion of the aldehydes approximated 79%.

EXAMPLE 8

Unsaturated aldehydes representative of product from oxo and aldol reactions of Dimate ® hexenes as produced in Example 7, were subjected to hydrogenation. An autoclave was charged with 130.95 g of 45%+5% cobalt on Kieselguhr, 1336.1 grams of the aldol condensation product and hydrogen to 1500 psi gauge (10,644 KPa). The autoclave was carefully heated to 160° C., with gas uptake starting at 100° C. The pressure and temperature were maintained for 4½ hours. The catalyst ws filtered off and washed with methanol to remove any residual alcohols. The material was then distilled using a 30 cm. vigreux column at 5 mm Hg. The $C_{14}$ alcohols were collected from 119° to 122° C. From analysis of the aldehydes prior to the aldol reaction, and analysis of derivatives of some of the alcohol components, together with gas chromatographic and other identification as included and described hereinbelow, it was concluded that the product includes some 28 alcohols in amounts and as named and illustrated by skeletal structure in Table 3 where the hydroxyl-bearing group is designated by an asterisk.

TABLE 3

| Structure | Tetradecanols Name | Weight % |
|---|---|---|
| C C C C C C C C C C<br>    C      C*   C | 2-(3-methylbutyl)-5-methyloctanol | 25.4 |
| C C C C C C C C C C<br>  C       C* | 2-(1-methylbutyl)-5-methyloctanol | 14.8 |

TABLE 3-continued

| Tetradecanols Structure | Name | Weight % |
|---|---|---|
| C C C C C C C C C C C<br>    C      C* | 2-pentyl-5-methyloctanol | 13.4 |
| C C C C C C C C C C C<br>    C      C*   C | 2-(3-methylbutyl)7-methyloctanol | 7.0 |
| C C C C C C C C C C C C<br>        C* | 2-pentylnonanol | 6.0 |
|     C<br>C C C C C C C C C<br>    C     C*   C | 2-(3-methylbutyl)-5-,6-dimethylheptanol + | |
|    C     C<br>C C C C C C C C C<br>        C* | 2-(1-methylbutyl)5,6-dimethylheptanol | 5.1 |
| C C C C C C C C C C C<br>    C      C* | 2-pentyl-7-methyloctanol | 4.1 |
| C C C C C C C C C C C C<br>      C*   C | 2-(3-methylbutyl)-nonanol | 4.1 |
|    C<br>C C C C C C C C C C<br>    C      C* | 2-(1-methylbutyl)-7-methyloctanol | 2.4 |
| C C C C C C C C C C C<br>     C   C* | 2-pentyl-4-methyloctanol | 2.4 |
| C C C C C C C C C C C C<br>    C      C* | 2-pentyl-5,6-dimethylheptanol | 2.3 |
|    C<br>C C C C C C C C C C<br>      C   C*   C | 2-(3-methylbutyl)-4-methyloctanol | 2.2 |
| C C C C C C C C C C C | 2-(1-methylbutyl)-nonanol | 1.5 |
| C C C C C C C C C C C C<br>        C* | 2-(1-methylbutyl)-nonanol | 1.5 |
|    C<br>C C C C C C C C C<br>      C   C*<br>   C | 2-(1-methylbuty)-4-ethylheptanol | 0.7 |
| C C C C C C C C C C C C<br>      C   C*<br>      C | 2-pentyl-4-ethylheptanol | 0.6 |
|      C<br>C C C C C C C C C C C<br>        C*  C | 2-(1,2-dimethylpropyl)-nonanol | 0.5 |

TABLE 3-continued

| Tetradecanols Structure | Name | Weight % |
|---|---|---|
|        C<br>C C C C C C C C C C C<br>    C     C* | 2-(1-methylbutyl)-4-methyloctanol | 0.4 |
|      C     C<br>C C C C C C C C C C<br>    C     C*   C | 2-(1,2-dimethylpropyl)-5,6-dimethylheptanol | 0.4 |
| C C C C C C C C C C<br>    C     C*   C<br>    C | 2-(3-methylbutyl)-4-ethylheptanol | 0.2 |
|      C<br>C C C C C C C C C C C<br>    C     C*   C | 2-(1,2-dimethylpropyl)-7-methyloctanol | UNK |
|      C<br>C C C C C C C C C C<br>    C     C*   C | 2-(1,2-dimethylpropyl)-5-methyloctanol | UNK |
|      C<br>C C C C C C C C C C<br>    C     C*   C | 2-(1,2-dimethylpropyl)-4-methyloctanol | UNK |
|      C<br>C C C C C C C C C<br>    C   C*   C | 2-(1,2-dimethylpropyl)-2-ethylheptanol | UNK |
| C C C C C C C C C C C<br>    C    C*   C | 2-pentyl-4,6-dimethylheptanol | UNK |
| C C C C C C C C C C<br>    C   C   C*   C | 2-(3-methylbutyl)-4,6-dimethylheptanol | UNK |
|      C<br>C C C C C C C C C<br>   C   C   C*   C | 2-(1,2-dimethylpropyl)-4,6-dimethylheptanol | UNK |
|      C<br>C C C C C C C C C<br>   C   C   C* | 2-(1-methylbutyl)-4,6-dimethylheptanol | UNK |

Chromatographic retention times for particular alcohols, both as components of a mixture and from individual synthesis, are set forth in Table 4, together with the aldehyde pair involved in the synthesis.

TABLE 4

TETRADECANOLS GC IDENTIFICATION

| Name | Retention Time In Mixture | Aldol Condensation Substrates | | Retention Time From Individual Synthesis |
|---|---|---|---|---|
| | | Carbanion | Acceptor | |
| 2-(3-methylbutyl)-5-methyloctanol | 31.99 | 5-methylhexanal | 3-methylhexanal | 32.36 |
| | 32.55 | | | 32.43 |
| 2-(1-methylbutyl)-5-methyloctanol | + | 3-methylhexanal | 3-methylhexanal | — |
| | 32.74 | | 32.60 | |
| 2-pentyl-5-methyloctanol | 36.62 | Heptanal | 3-methylhexanal | 36.49 |
| 2-(3-methylbutyl)-7-methyloctanol | 33.32 | 5-methylhexanal | 5-methylhexanal | 33.27 |
| 2-pentylnonanol | 43.60 | Heptanal | Heptanal | 43.44 |
| 2-(3-methylbutyl)-5,6-dimethylheptanol | 31.27 | 5-methylhexanal | 3,4-dimethylhexanal | 31.24 |
| 2-(1-methylbutyl)-5-,6-dimethylheptanol | 31.27 | 3-methylhexanal | 3,4-dimethylpentanal | 31.28 |
| | 37.86 | | | 37.93 |
| 2-pentyl-7-methyloctanol | or | Heptanal | 5-methylhexanal | or |

TABLE 4-continued
TETRADECANOLS GC IDENTIFICATION

| Name | Aldol Condensation Substrates Carbanion | Acceptor | Retention Time From Individual Synthesis |
|---|---|---|---|
| 2-(3-methylbutyl)-nonanol | 38.18<br>37.86<br>or<br>5-methyl-<br>hexanal | Heptanal or | 38.29<br>37.93 |
| 2-(1-methylbutyl)-7-methyloctanol | 38.18<br>34.17<br>+<br>34.40<br>Retention<br>Time<br>In Minutes | 3-methylhexanal | 5-methylhexanal | 38.29<br>34.31<br>+<br>34.50 |
| 2-pentyl-4-methyloctanol | 34.17<br>+<br>34.40 | Heptanal | 2-methylhexanal | 34.15<br>+<br>34.41 |
| 2-pentyl-5,6-dimethylheptanol | 35.79 | Heptanal | 3,4-dimethylpentanal | 35.82 |
| 2-(3-methybutyl)-4-methyloctanol | 29.85<br>+<br>30.11 | 5-methylhexanal | 2-methylhexanal | 29.84<br>+<br>30.09 |
| 2-(1-methylbutyl)-nonanol | 38.98<br>+<br>39.13 | 3-methylhexanal | Heptanal | 38.89<br>+<br>39.04 |
| 2-(1-methylbutyl)-4-ethylheptanol | 26.67<br>+<br>26.95 | 3-methylhexanal | 2-ethylpentanal | 26.67<br>+<br>27.05 |
| 2-pentyl-4-ethylheptanol | 33.05 | Heptanal | 2-ethylpentanal | 32.97 |
| 2-(1,2-dimethylpropyl)-nonanol | 30.11<br>30.40 | 3,4-dimethylpentanal | Heptanal | 30.58<br>30.38 |
| 2-(1-methylbutyl)-4-methyloctanol | +<br>30.84 | 3-methylhexanal | 2-methylhexanal | +<br>30.83 |
| 2-(1,2-dimethylpropyl)-5,6-dimethylheptanol | 27.82<br>+<br>28.86 | 3,4-dimethylpentanal | 3,4-dimethylpentanal | 27.79<br>+<br>28.73 |
| 2-(3-methylbutyl)-4-ethylheptanol | +<br>29.13<br>28.86<br>+<br>28.97 | 5-methylhexanal | 2-ethylpentanal | +<br>29.01<br>28.87<br>+<br>28.89 |
| 2-(1,2-dimethylpropyl)-7-methyloctanol | | 3,4-diemthylpentanal | 5-methylhexanal | |
| 2-(1,2-dimethylpropyl)-5-methyloctanol | | 3,4-dimethylpentanal | 3-methylhexanal | |
| 2-1,2-dimethylpropyl)-4-methyloctanal | | 3,4-dimethylpentanal | 2-methylhexanal | |
| 2-(1,2-dimethylpropyl)-2-ethylheptanol | | 3,4-dimethylpentanal | 2-ethylpentanal | |
| 2-pentyl-4,6-dimethylheptanol | | Heptanol | 2,4-dimethylpentanal | |
| 2-(3-methylbutyl)-4,6-dimethylheptanol | | 5-methylhexanal | 2,4-dimethylpentanal | |
| 2-(1,2-dimethylpropyl)-4,6-dimethylheptanol | | 3,4-dimethylpentanal | 2,4-dimethylpentanal | |
| 2-(1-methylbutyl)-4,6-dimethylheptanol | | 3-methylhexanal | 2,4-dimethylhexanal | |

Carbanion and acceptor columns present the two aldehydes that were used in aldos to prepare the respective alcohol.

The identification and reported percentage composition of the product alcohols were accomplished by utilizing gas-liquid chromatography (G.C.) coupled with synthesis of the isomers. The individual alcohols were synthesized by aldol condensation of pure heptanal aldehyde isomers followed by hydrogenation to the alcohol. The heptanal pairs can be reacted together with the procedure of Example 7 above. The elution time of the individual derivatized isomers were then matched with peak-elution times in the product mixture to identify the compounds in the mixture. Verification of the structures was accomplished by several methods. Gas chromatography combined with mass spectrometry (G.C.-MS) was used to show that the mixture contained only tetradecanol isomers. The logic by which we synthesized the various alcohol isomers, discussed above, was confirmed in three cases by $^{13}C$ nuclear magnetic resonance (nmr) and also in one case by a single crystal X-ray structural determination of a solid derivative. Thus, the structures of 2-pentylnonanol, 2-(1-methylbutyl)-5-methyl-octanol and 2-(3-methylbutyl) 7-methyloctanol were unambiguously identified using two dimensional double quantum coherence $^{13}C$ nmr techniques (G. Bodenhause, "Progress in NMR Spectrocscopy," 14, 137 (1981). In addition, the $\beta$-napthyl sulfonate ester of 2-(3-methylbutyl-7-methyl octanol was prepared (m. pt 47°) and a single crystal suitable for X-ray crystallographic investigation was grown. A single crystal study was performed using copper K$\alpha$ radiation with a Syntex P2$_1$ diffractometer. The space group was found to be P2$_1$/N. Cell constants were $= 8.186(1)$, $b = 29.958(7)$, $c = 10.316(2)$ Å; $a = 107.49(2)°$; $Z = 4$; $M = 404.62$. The structure was solved by direct methods and refined to a final R value of 0.091 using 2586 observed reflections. The structure is shown in the accompanying FIG. 1. The bond lengths and bond angles are given in Table 5.

This X-ray determination unequivocally confirms the backbone structure of the alcohol as 2-(3-methylbutyl)-7-methyl octanol.

TABLE 5
Bond Lengths and Bond Angles in the $\beta$-Naphthyl Sulfonate Ester of 2-(3-methylbutyl-7-methyl Octanol
(Numbering system used here is shown in FIG. 1)

Bond Lengths

TABLE 5-continued

Bond Lengths and Bond Angles in the β-Naphthyl Sulfonate Ester of 2-(3-methylbutyl-7-methyl Octanol (Numbering system used here is shown in FIG. 1)

| | |
|---|---|
| S1 - 02 | 1.565 A |
| S1 - 011 | 1.427 |
| S1 - 012 | 1.427 |
| 02 - C3 | 1.493 |
| C3 - C4 | 1.543 |
| C4 - C5 | 1.526 |
| C4 - C23 | 1.538 |
| C5 - C6 | 1.534 |
| C6 - C7 | 1.542 |
| C7 - C8 | 1.544 |
| C8 - C9 | 1.573 |
| C9 - C10 | 1.574 |
| S1 - C14 | 1.747 |
| C13 - C14 | 1.392 |
| C13 - C18 | 1.399 |
| C14 - C15 | 1.421 |
| C15 - C16 | 1.347 |
| C16 - C17 | 1.416 |
| C17 - C22 | 1.417 |
| C18 - C19 | 1.442 |
| C20 - C21 | 1.449 |
| C21 - C22 | 1.372 |
| C23 - C24 | 1.545 |
| C24 - C25 | 1.564 |
| C25 - C26 | 1.540 |
| C25 - C27 | 1.393 |
| Bond Angles | |
| 02 - S1 - 011 | 104.1° |
| 02 - S1 - 012 | 109.8 |
| 02 - S1 - C14 | 103.3 |
| 011 - S1 - 012 | 119.9 |
| 011 - S1 - C14 | 108.9 |
| 012 - S1 - C14 | 109.5 |
| S1 - 02 - C3 | 117.9 |
| 02 - C3 - C4 | 106.0 |
| C3 - C4 - C5 | 111.4 |
| C3 - C4 - C23 | 113.2 |
| C5 - C4 - C23 | 109.4 |
| C4 - C5 - C6 | 115.8 |
| C5 - C6 - C7 | 110.1 |
| C6 - C7 - C8 | 110.6 |
| C7 - C8 - C9 | 111.7 |
| C8 - C9 - C10 | 112.5 |
| C8 - C9 - C28 | 106.8 |
| C10 - C9 - C28 | 112.4 |
| C14 - C13 - C18 | 118.6 |
| S1 - C14 - C13 | 119.9 |
| S1 - C14 - C15 | 118.6 |
| C13 - C14 - C15 | 121.6 |
| C14 - C15 - C16 | 119.6 |
| C15 - C16 - C17 | 121.5 |
| C16 - C17 - C18 | 118.4 |
| C16 - C17 - C22 | 122.5 |
| C18 - C17 - C22 | 119.1 |
| C13 - C18 - C17 | 120.3 |
| C13 - C18 - C19 | 120.0 |
| C17 - C18 - C19 | 119.6 |
| C18 - C19 - C20 | 119.8 |
| C19 - C20 - C21 | 120.2 |
| C20 - C21 - C22 | 120.6 |
| C17 - C22 - C21 | 120.6 |
| C4 - C23 - C24 | 113.6 |
| C23 - C24 - C25 | 112.1 |
| C24 - C25 - C26 | 108.2 |
| C24 - C25 - C27 | 119.2 |
| C26 - C25 - C27 | 114.3 |

In FIG. 1, the β-napthylsulfonate ester of 2-(3-methylbutyl)-7-methyl octanol is shown. The sulfur and oxygen atoms are identified by as S and O respectively, while all other atoms are carbon. The portion of the structure below the oxygen atom 2 is the carbon structure of the alcohol, while that above 2 is the naphthylsulfonate portion of the derivative.

The gas chromatography for the retention procedures discussed was done with acetate ester derivatives. The acetate esters were prepared by utilizing 0.1 cc of alcohol sample, 0.3 cc acetic anhydride, 1 drop of pyridine, and heating in a sealed vial for 10 minutes at 100° C. The product was injected directly into a gas chromatogram, which was a Varian 3700 with splitter for glass capillary columns, Flame ionization detector and Hewlett-Packard 3352 computer. Details of the column and procedure were:

| | |
|---|---|
| SP-2100 Glass capillary column 60 meter length × 0.25 mm internal diameter, 27.1 cm/sec helium: | |
| Injection/splitter | 280° C. |
| Detector | 280° C. |
| Column oven | Progress from 120° C. to 150° C. at 2° C./minute, and held at 150° C. |
| Detector Sensitivity | Range $10^{-11}$ amps/millimole |
| Injection Size | 0.06 ul/split 60:1 |

Figure 2:
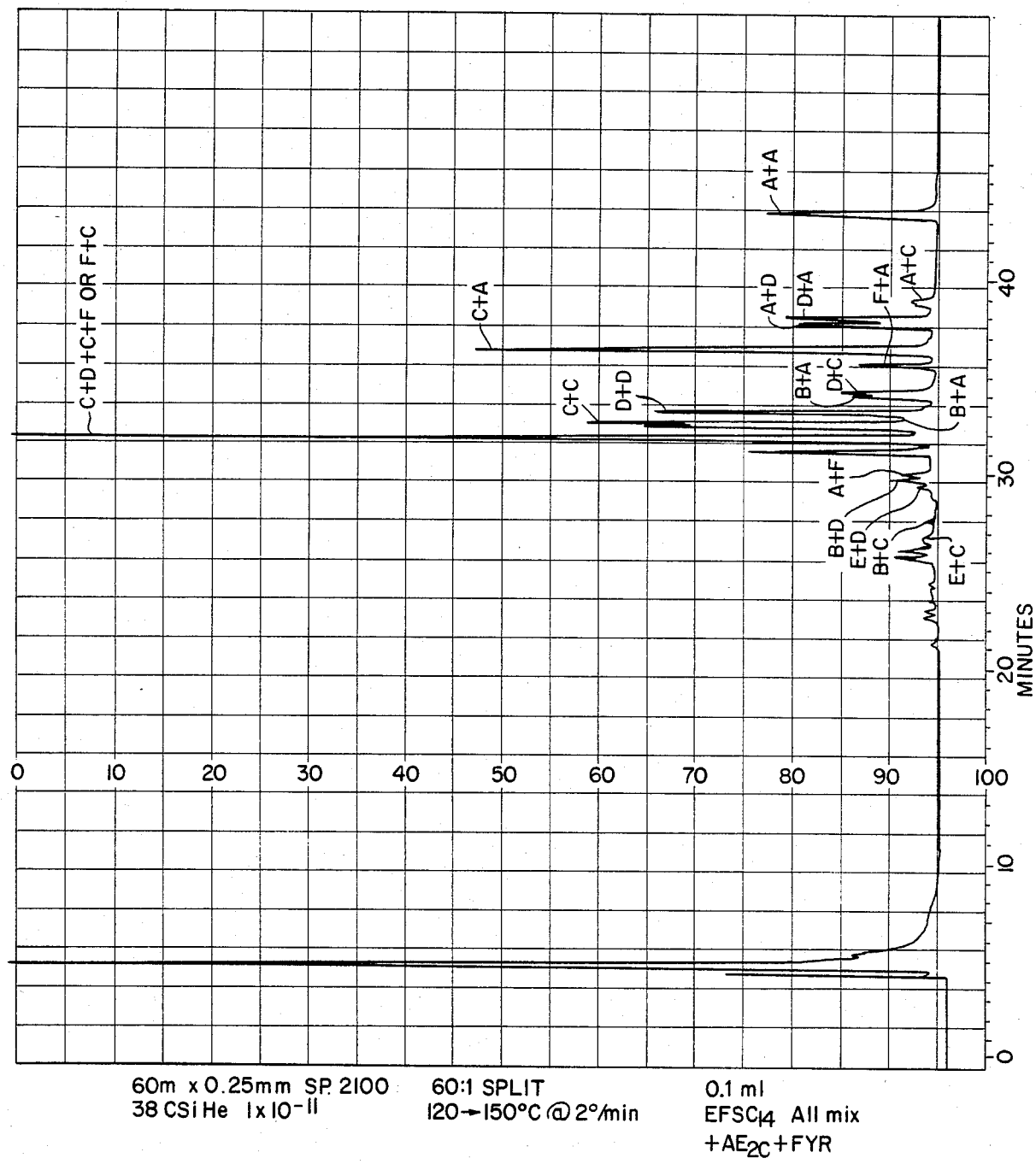

A typical chromatograph of the acetate derivative of the mixture of alcohols of Table 3, obtained by the foregoing procedure, is shown in FIG. 2 in which retention time is measured on the horizontal axis in minutes. The chromatograph was made at a chart speed of 5 mm/minute and covers from time zero to over 50 minutes. The designations of several peaks by combinations of two letters indicate the aldehydes combined in the aldol stage of the product formation, with the letters symbolizing:

| | |
|---|---|
| A = | n-heptanal |
| B = | 2-methylhexanal |
| C = | 3-methylhexanal |
| D = | 4-methylhexanal |
| E = | 2-ethylpentanal |
| F = | 2,3-dimethylpentanal |

EXAMPLE 9

This example demonstrates an aldool condensation of heptanal in glassware under conventional aldol conditions. The reaction flask was charged with 116 ml of 0.8 M NaOH and the heptanal, 371.03 g., placed into the addition funnel. The system was kept under a nitrogen blanket and the agitation was set at 500 rpm. The reaction flask was heated to reflux, and the heptanal added at a constant rate such that the addition was completed after 230 minutes. A sample was removed to compare with conventional aldol results and only 33.5% of the upper phase of the sample was $C_{14}$ unsaturated aldehyde and 61% was unreacted heptanal. The system was held at reflux for an additional 10 hours after which the system was cooled. The lower phase was removed, 135.74 g, and the upper phase, 336.06 g., was found to contain 66.5% 2-pentylnon-2-enal, 26.4% unreacted heptanal and 2.5% heptanol.

EXAMPLE 10

This example demonstrates the efficacy of using a co-solvent with the water to enhance the aldol reaction of heptanal. The reaction flask was charged with 31 ml of 0.9M NaOH and 100 ml methanol. The addition funnel was charged with 115 g. of heptanal under a nitrogen blanket. The aqueous-methanol mixture was heated to reflux with agitation of 450 rpm. The heptanal was added over a 40 minute period and refluxed for an additional 90 minutes. The system was cooled and the lower phase removed. The upper phase contains 10.1% methanol, 84.0% 2-pentylnon-2-enal, 2.0% unreacted heptanal and 1.2% heptanol. This represents 94% conversion with 98% selectivity. The tetradecenals were hydrogenated as in Example 8 and the resulting saturated alcohols were treated as in example 8 including filtration and distillation.

The use of methanol in this procedure was effective as a cosolvent, as compared to Example 9 where a cosolvent was not used.

EXAMPLE 11

Dimerization of propylene over transition metal catalysts produces a mixture of hexenes.

The linear hexenes in the mixture can be separated and such linear hexenes are for the most part 2-hexenes. The folling procedure illustrates the reaction of linear 2-hexenes in an oxo reaction, followed by an aldol reaction of the product. A sample of refinery 2-hexenes was passed through basic alumina particles for removal of oxides and 802 grams of the hexenes was placed in a 1 gallon stainless steel autoclave with 4.75 grams $Co_2(CO)_8$ catalyst. The autoclave was pressured to 2400 psi gauge with 1:1 carbon monoxide and hydrogen, and heated to 110° C. The temperature was kept at about 110° C. for 1 hour and then rose to about 130° as the procedure was continued for about 5 hours. A 916.5 gram product was obtained, with conversion about 94% with about 78% selectivity to $C_7$ compounds, and 71.5% to $C_7$ aldehydes. Chromatography indicated the aldehydes were in ratio of about 29.4 n-heptanal to 16.7 2-methylhexanal to 8.5 2-ethylpentanal. A 907 gram amount of the product was distilled, with a final pot temperature of 120° C., and vacuum of 3 mm Hg. to obtain a 608 gram distillation fraction and 278 gram residue. Chromatography indicated the fraction included $C_7$ aldehydes in ratio 33.4 n-heptanal to 26.8 2-methylhexanal to 17.2 2-ethylpentanal, and minor amounts of other components. Evidently there was more loss of the normal aldehyde than the branched ones in the distillation.

It is feasible to achieve a higher percentage of n-aldehyde than present in the above distillation fraction, such as 60% or better, and therefore n-heptanal was added to the above fraction to have a more typical aldehyde for aldol reaction about 600 grams of the above fraction being used with 500 grams n-heptanal. A 300 ml amount of 0.8 molar sodium hydroxide was placed in a reaction flask with 955 ml methanol, and the aldehydes were placed in an addition funnel. The reaction medium was heated to about 71° C., and addition was slowly started and completed in about 13 hours. Chromatography indicated about 50% completion of the reaction, with $C_{14}$ aldehydes in ratio of about 23.4% 2-pentylnon-2-enal to 8.72% 2-penthyl-4-methyloct-2-enal to 1.4% 2-pentyl-4-ethylhept-2-enal. Several $C_7$ aldehydes were also present in the ratio of 22.0 heptanal to 8.5 2-methylhexanal to 5.3 2-ethylpentanal.

The aldol condensation product was hydrogenated over a cobalt on Kieselguhr catalyst, using 131 grams catalyst with 1336 grams of the condensation product. The materials were maintained at about 160° C. and 1500 psi gauge (10,645 KPa) of hydrogen for about two hours when reaction appeared complete. Reaction conditions were maintained for an additional 4.5 hours. Analysis indicated about 99% completion of the hydrogenation. The product contained 2-pentyl-nonanol in about 18.4 to 7.2 ratio to a mixture of 2-pentyl-5-methyl- octanol and 2-pentyl-4-ethyl-heptanol and large amounts of $C_7$ alcohols from the unreacted aldehyde, being heptanol in a 27.5 to 16.3 ratio to a mixture of 2-methylhexanol and 2-ethylpentanol. The product was fractionated by distillation, with a 280 gram fraction being obtained at 110°–115° C. at 2 mm Hg from 1180 grams of hydrogenation product. The fraction was in large predominance composed of $C_{14}$ alcohols.

EXAMPLE 12

A mixture of hexenes produced by the Dimersol® dimerization process was utilized as olefin reactant. The crude hexene cut from the dimerization was used, and had the distribution of linear and branched hexenes typical of such material. A 1029 gram amount of the hexenes was used in a 1 gallon autoclave with 6.04 grams catalyst, $Co_2(CO)_8$, 0.02 weight %. Peroxides had been removed from the hexenes by treatment on a basic alumina column. The autoclave was taken to reaction conditions with 1:1 $CO/H_2$ and maintained at 110° C. and 2600 psi gauge (18028 KPa) for 9 hours, with 80% of theoretical gas uptake, and then continued overnight. Chromatography indicated high conversion to $C_7$ aldehydes, with minor amounts of residual hexenes. A 1360 gram amount of the product was subjected to distillation, with a 797 gram fraction being obtained at pot temperatures of 60° to 97° C. as the vacuum dropped from 90 mm Hg to 5 mm Hg. Chromatography indicated a high portion of $C_7$ aldehydes with a very small amount of $C_6$ olefins.

A 792 gram amount of the above aldehyde fraction was utilized in an aldol reaction, adding the aldehyde material from an addition funnel to a reaction flask containing 564 grams methanol and 250.9 grams 0.8 molar sodium hydroxide. The addition took 6 hours, with stirring at about 500 rpm and temperature at 72°–73° C. The reaction mixture was then refluxed for 1.5 hours. Analysis of a sample indicated only about 1 part aldol product to 3 parts aldehyde, on a mole basis. The reaction was continued at reflux overnight, giving 1 part aldol product to about 2.6 parts aldehyde reactant. During the reaction it was observed that the reaction mixture had a large upper phase and a smaller lower phase, indicating that methanol was not very effective in promoting miscibility and reaction, possibly because of the relatively long chain length of $C_7$ aldehydes. Chromatography showed a fair amount of the $C_{14}$ aldol product, including 2-pentylnonenal, and a large amount of unreacted $C_7$ aldehydes. (Results were better in Example 10 above in which a higher proportion of methanol was employed).

The above aldol product was subjected to further aldol reaction, after removing the methanol to employ different conditions. A 552 gram amount of the aldol condensate, 55.6 area percent $C_7$ aldehydes and 31.5 area percent $C_{14}$ enals, was placed in an addition funnel and added to a reaction flask containing 163 grams 0.8M NaOH and 389 grams 2,5-hexanediol. Addition was complete after 45 minutes, with temperature maintained at 100° C. with agitation of the reaction mixture. The reaction mixture was then refluxed at 100° C. for 1.75 hours. The reaction mixture separated into upper and lower phases of about equal weight. The conversion had been improved in that the ratio of $C_{14}$ enals to $C_7$ aldehydes in the product (upper phase) was now about 1.7 to 1.

A 515 gram amount of the product was subjected to hydrogenation, employing 51.65 grams cobalt on Kieselguhr catalyst and 160° C., about 1580 psi gauge (10,995 KPa) hydrogen. Approximately 549 grams of product was recovered. The conversion of $C_{14}$ saturated alcohols was about 90%, with about 10% found as unsaturated alcohols. The product was filtered to remove catalyst, and the filtrate was distilled. The process produced several $C_{14}$ alcohols in very substantial amounts, with a number of others in very small amounts. Several $C_7$ alcohols from unreacted aldehyde were also present in substantial amount.

Another sample of hexenes product from a Dimersol® dimerization refinery product was analyzed and found to have the following distribution:

| Hexene Distribution | % (100% Basis) | |
|---|---|---|
| 2,3-dimethyl-2-butene | 6.4 | |
| 2-methyl-2-pentene | 39.2 | |
| trans-4-methyl-2-pentene | 15.9 | |
| cis-4-methyl-2-pentene | 2.9 | |
| 2-methyl-1-pentene | 5.0 | |
| 2,3-dimethyl-1-butene + 4-methyl pentene | 1.7 | |
| trans-2-hexene | 16.5 | |
| trans-3-hexene | 5.8 | 28.9 |
| cis 3 + cis 2-hexene | 5.6 | |
| 1-hexene | 1.0 | |

The hexenes are suitable for conversion to detergent alcohol in accord with the present invention.

Nonionic detergents prepared from the present alcohols by ethoxylation were tested for detersive efficiency in comparison with reference compounds which were subbstantially normal alcohol ethoxylates, being Neodol® ethoxylates marketed by Shell Chemical Company. The reference compound alcohols, produced by ethylene oligomerization, are composed of designated percentages of normal alcohols, generally in the range of 70 to 80%, and the remainder of isomeric 2-alkyl (predominantly 2-methyl) primary alcohols. The tests employed are recognized tests in which a fabric soiled with synthetic sebum/airborne particulate is washed and the results measured by Rd, change in reflectance by Gardner XL-23 Color Difference meter. Tests were conducted with a polyester-cotton blend fabric containing 65% polyester, and with a cotton broadcloth fabric. Three different ethoxylates of the $C_{14}$ alcohol mixture of the present invention (designated $C_{14}$ Aldol) were used, having 6.0, 8.7 and 10.5 ethoxylate groups on the average. The reference compounds for comparison were Neodol 45 ethoxylates having 7 and 13 ethoxyl groups, and Neodol 25 ethoxylates having 7 and 12.5 ethoxyl groups. An individual oxo-aldol $C_{14}$ alcohol of the present invention was also tested 2-(1-methylbutyl)-5-methyloctanol. It was prepared by aldol of 3-methylheptanol, and is designated as $C_{14}$ High Vicinal, because of presence of adjacent branches in its structure. The results are reported in Tables 5-a, 5-b, 5-c, 5-d, and 5-e. The tables include results with the detergent including sodium tripolyphosphate (STP) builder, sodium carbonate builder, or no builder, and a washing temperature of 120° F. in most instances, but 75° F. in Table 5-d. Tests were reported at different amounts of water hardness as set forth. The sodium tripolyphosphate built detergent, for example, had a composition of 10% of the nonionic (surfactant), 24% sodium tripolyphosphate, 12% R.U. Sebacate (as is), 53% sodium sulfate, and 1% sodium carboxyethyl cellulose, while the one with no builder was similar, with the STP replaced by additional sodium sulfate. The detergent was used in concentration 0.15%, for anionic concentration of 150 ppm. Water hardness was from a 3/2 atom ratio of calcium and magnesium ions, with concentration calculated as parts per million by weight of calcium carbonate.

TABLE 5a

Synthetic Sebum Detergency
120° F., Cotton Δ Rd
30% $Na_2CO_3$ Builder System

| Sample | Water Hardness | | | |
|---|---|---|---|---|
| | 0 | 50 ppm | 100 ppm | 200 ppm |
| Neodol 45-7 | 32.5 | 31.5 | 29.6 | 17.2 |
| Neodol 45-13 | 32.3 | 31.1 | 29.2 | 23.3 |
| Neodol 25-7 | 31.8 | 29.9 | 28.8 | 23.9 |
| Neodol 25-12.5 | 33.1 | 30.7 | 27.6 | 20.2 |
| $C_{14}$ Aldol 6.0 | 32.7 | 29.4 | 26.0 | 9.8 |
| $C_{14}$ Aldol 8.7 | 32.6 | 30.8 | 27.0 | 24.0 |
| $C_{14}$ Aldol 10.5 | 31.5 | 31.1 | 28.0 | 26.2 |
| $C_{14}$ High Vicinal 5.5 | 20.8 | 20.6 | 18.8 | 1.4 |
| 9.5 | 19.5 | 18.9 | 19.4 | 4.8 |
| 13.3 | 15.5 | 17.0 | 15.8 | 1.1 |

TABLE 5b

Synthetic Sebum Detergency
120° F., cotton, Δ Rd
0% Builder System

| Sample | Water Hardness | | | |
|---|---|---|---|---|
| | 0 | 50 ppm | 100 ppm | 200 ppm |
| Neodol | 31.5 | 29.5 | 26.1 | 14.0 |
| Neodol | 31.4 | 31.3 | 29.5 | 17.8 |
| Neodol 25-7 | 31.7 | 29.4 | 26.1 | 14.8 |
| Neodol 25-12.5 | 30.1 | 31.1 | 29.7 | 25.9 |
| $C_{14}$ Aldol 6.0 | 30.4 | 26.0 | 20.7 | 6.8 |
| $C_{14}$ Aldol 8.7 | 30.2 | 30.6 | 24.5 | 22.4 |
| $C_{14}$ Aldol 10.5 | 30.4 | 30.9 | 26.3 | 24.7 |
| $C_{14}$ High Vicinal 5.5 | 32.7 | 18.9 | 21.0 | 3.9 |
| 9.5 | 32.1 | 20.1 | 20.3 | 7.4 |
| 13.3 | 32.6 | 17.5 | 16.1 | 4.3 |

TABLE 5-c

Synthetic Sebum Detergency
120° F., Cotton, Δ Rd
24% STP Builder System

| Sample | Water Hardness | | | |
|---|---|---|---|---|
| | 0 | 50 ppm | 100 ppm | 200 ppm |
| Neodol 45-7 | 32.2 | 34.2 | 35.2 | 26.9 |
| Neodol 45-13 | 31.5 | 34.0 | 35.0 | 28.9 |
| Neodol 25-7 | 32.2 | 34.4 | 34.5 | 26.1 |
| Neodol 25-12.5 | 31.7 | 33.5 | 34.5 | 27.4 |
| $C_{14}$ Aldol 6.0 | 31.4 | 34.4 | 34.5 | 20.5 |
| $C_{14}$ Aldol 8.7 | 30.8 | 33.5 | 35.7 | 23.5 |
| $C_{14}$ Aldol 10.5 | 31.4 | 34.3 | 34.8 | 25.2 |
| $C_{14}$ High Vicinal 5.5 | 32.8 | 35.3 | 36.6 | 22.4 |
| 9.5 | 32.8 | 33.5 | 35.8 | 25.3 |
| 13.3 | 32.7 | 25.1 | 34.5 | 24.9 |

TABLE 5-d

Synthetic Sebum Detergency
75° F., PE/cotton, Δ Rd
24% STP Builder System

| Sample | Water Hardness | | | |
|---|---|---|---|---|
| | 0 | 50 ppm | 100 ppm | 200 ppm |
| Neodol 45-7 | 18.3 | 17.7 | 15.7 | 4.0 |
| Neodol 45-13 | 16.7 | 16.1 | 15.1 | 1.9 |
| Neodol 25-7 | 18.8 | 19.8 | 18.0 | 4.3 |
| Neodol 25-1.25 | 16.5 | 17.2 | 14.5 | 3.7 |
| $C_{14}$ Aldol 6.0 | 19.8 | 17.7 | 19.3 | 3.4 |
| $C_{14}$ Aldol 8.7 | 19.3 | 18.2 | 20.0 | 5.0 |

TABLE 5-d-continued

Synthetic Sebum Detergency
75° F., PE/cotton, Δ Rd
24% STP Builder System

| Sample | Water Hardness | | | |
|---|---|---|---|---|
| | 0 | 50 ppm | 100 ppm | 200 ppm |
| $C_{14}$ Aldol 10.5 | 17.5 | 18.1 | 16.6 | 14.0 |
| $C_{14}$ High | | | | |
| Vicinal 5.5 | 20.8 | 20.6 | 18.8 | 11.4 |
| 9.5 | 19.5 | 18.9 | 19.4 | 14.8 |
| 13.3 | 15.5 | 17.0 | 15.8 | 11.1 |

TABLE 5-e

Synthetic Sebum Detergency
120° F., PE/cotton, Δ Rd
24% STP Builder System

| Sample | Water Hardness | | | |
|---|---|---|---|---|
| | 0 | 50 pm | 100 ppm | 200 ppm |
| Neodol 45-7 | 19.8 | 19.7 | 18.7 | 16.2 |
| Neodol 45-13 | 18.6 | 17.8 | 16.8 | 12.8 |
| Neodol 25-7 | 19.9 | 19.6 | 20.4 | 16.7 |
| Neodol 25-12.5 | 18.1 | 17.8 | 16.6 | 13.4 |
| $C_{14}$ Aldol 6.0 | 19.8 | 19.0 | 18.6 | 7.9 |
| $C_{14}$ Aldol 8.7 | 19.9 | 21.7 | 21.1 | 18.9 |
| $C_{14}$ Aldol 10.5 | 20.1 | 18.8 | 19.6 | 17.6 |
| $C_{14}$ High | | | | |
| Vicinal 5.5 | 21.2 | 18.9 | 21.0 | 13.9 |
| 9.5 | 19.4 | 20.1 | 20.3 | 17.4 |
| 13.3 | 18.4 | 17.5 | 16.1 | 14.3 |

It can be seen that the ethoxylates of the present alcohol mixture are in general comparable in the tests of detersive efficiency to the established reference ethoxylates. It can be noted that in some respects the present compounds give better results, as for example with the 8.7 ethoxylate in Tables 5-d and 5-e involving tests with polyester/cotton.

The $C_{14}$ mixed alcohol product of the present invention, in ethoxylate form, was tested for biodegradability, in comparison to commercial detergents. The test procedure used was the semi-continuous activated sludge test which determines dissolved organic carbon as the measure of biodegradation. The results are reported in Table 6 below. The aldol-alcohol ($C_{14}$) was the alcohol mixture as described in Table 4 above, which has been ethoxylated to have an average of 10.5 ethoxyl groups. It was compared to a Neodol 25-12, which is an ethoxylate of an approximately linear alcohol in the 12 to 15 carbon range, with an average of 12 ethoxyl groups. The two LAS reference compounds are linear alkyl benzene sulfonates of a type utilized commercially. The test-measures the removal of dissolved organic carbon (DOC), and is a measure of complete degradation of the compounds.

While the degradation of the aldol product was not as fast as that of the linear alcohol product (Neodol 25-12), it was still comparable to the LAS compounds which are suitable for commercial use. Also, the essentially complete removal in the 72-hour cycles indicates there are no resistant fragments.

Further biodegradation tests were carried out utilizing the semi-continuous activated sludge test, and comparing a $C_{14}$ aldol isomeric mixture ethoxylate with an ethoxylate of a high vicinal alcohol, i.e, 3-(1-methylbutyl)-5-methylheptanol. The 24-hour cycle results for weeks 4, 5 and 6 are reported in Table 7, While the high vicinal alcohol degrades somewhat more slowly, its rate is still fairly close to that of the isomeric mixture which was shown to be comparable to commercial materials in Table 6. Moreover, results with the isomeric mixture indicate that good biodegradation can be obtained even with a substantial amount of the high vicinal alcohol present. The results in Table 7 provide a comparison of the materials tested, but may not be directly comparable to other tests, because of the low ethoxyl content which may have affected solubility, or possibly unexplained test variations.

TABLE 7

Semi-Continuous Activated Sludge Test

| | | (% DOC. Removal - 24 hr) | | |
|---|---|---|---|---|
| | | Week 4 | Week 5 | Week 6 |
| 1. | Neodol$^R$ 25-7 Reference compound | 88 ± 38 | 97 ± 13 | 96 ± 8 |
| 2. | $C_{14}$ + 6.0 Ethylene Oxide (Dimersol Hexene) | 61 ± 13 | 65 ± 31 | 72 ± 6 |
| 3. | High Vicinal Alcohol + 6.3 Ethylene Oxide (from 3-methylhexanal) | 66 ± 44 | 51 ± 39 | 63 ± 12 |

What we claim is:

1. A mixture of $C_{14}$ isomeric alcohols which are characterized as nine-carbon alkanol with a five-carbon alkyl group substituted on the 2-position thereof, and with additional branching in most of the isomers, with most of the additional branches being methyl groups, and further characterized as liquid at ambient temperature and having varying hydrocarbon hydrophobe moieties making the mixture suitable for formation of effective detergents therefrom, and further characterized by suitable biodegradability, alcohols further characterized in that the isomers are in proportions attainable from aldol and hydrogenation reactions of a $C_7$ aldehyde obtained by oxo reaction of propylene dimers.

2. The alcohol mixture of claim 1 in which the alcohols are characterized by the structure

TABLE 6

| | Mean % DOC Removal[1] (95% Confidence Limits) | | | |
|---|---|---|---|---|
| | 2nd through 5th Week of Tests | | 6th through 8th Week of Tests | |
| Test Compound | 24-Hour Cycle (16 data points) | 72-Hour Cycle (3 data points) | 24-Hour Cycle (12 data points) | 72-Hour Cycle (3 data points) |
| Neodol 25-12 Reference Compound | 90 ± 6 | 98 ± 7 | 97 ± 2 | 100 |
| A230 LAS Reference Compound | 83 ± 7 | 92 ± 11 | 89 ± 3 | 97 ± 8 |
| Dodecen-1 Derived LAS Reference Compound | 81 ± 13 | 82 ± 59 | 89 ± 6 | 93 ± 27 |
| Aldol Alcohol ($C_{14}$) Ethoxylate (10.5 EO) | 77 ± 6 | 92 ± 16 | 88 ± 5 | 100 ± 1 |

[1] Mean % DOC Removal = (DOC in Feed − Net DOC in Effluent) × 100/DOC in Feed
Net DOC in Effluent = Test Chamber DOC − Control Chamber DOC

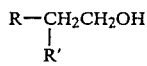

in which R is an alkyl group with 7 carbon atoms and R' is an alkyl group with 5 carbon atoms and in which in at least about 80% of the alcohols, R' is selected from n-pentyl, 3-methylbutyl and 1-methylbutyl, and R is selected from n-heptyl, 3-methylhexyl, 5-methylhexyl, 2-methylhexyl and 2-ethylpentyl groups.

3. The alcohols of claim 1 further characterized in that about 20 to about 35% of the alcohol have adjacent branches in their structure, but there are substantially no alcohols with genu substituents and therefore substantially no quaternary carbon.

4. An alcohol mixture of claim 1 having most of the alcohols represented by the structure:

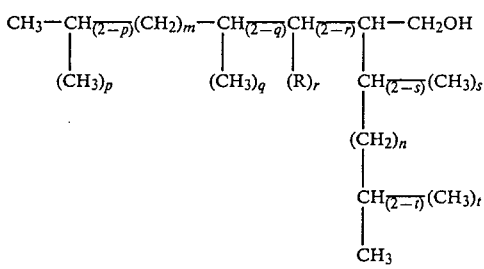

wherein:

R = methyl or ethyl;

p, q and r = 0 or 1; but only one of p, q and r can be 1;

m = 3, when p, q and r = 0;

m = 2, when r = 1 and R = methyl;

m = 1, when r = 1 and R = ethyl;

n = 2, when s and t = 0;

n = 1, when s or t = 1;

s and t = 0 or 1, but only one of s and t can be 1.

5. As a new compound, a $C_{14}$ alcohol suitable for use in formation of nonionic detergents and in liquid form, designated as 2-(3-methylbutyl)-5-methyl-octanol.

6. As a new compound, a $C_{14}$ alcohol suitable for use in formation of nonionic detergents and in liquid form, designated as 2-(1-methylbutyl)-5-methyloctanol.

7. As a new compound, a $C_{14}$ alcohol suitable for use in formation of nonionic detergents and in liquid form, designated as 2-pentyl-5-methyloctanol.

8. As a new compound, a $C_{14}$ alcohol suitable for use in formation of nonionic detergents and in liquid form, designated as 2-(3-methylbutyl)-7-methyloctanol.

9. The alcohol mixture of claim 1 further characterized as having alcohols present substantially in amounts as set forth in Table 3.

10. The alcohol mixture of claim 1 further characterized as comprised substantially of the alcohols of Table 4.

11. The alcohols of claim 1 in which the mixture is further characterized as comprising 28 isomers, including three main isomers which comprise 40 to 60% by weight of the isomeric mixture with 2-(3-methylbutyl)-5-methyloctanol being present in largest amount, followed by 2-(1-methylbutyl)-5-methyloctanol and 2-pentyl-5-methyloctanol, and in which about 65 to about 80% of the isomeric mixture is comprised of the aforesaid isomers together with 2-(3-methylbutyl)-7-methyloctanol, and 2-pentylnonanol, 2-pentyl-7-methyloctanol and 2-(3-methylbutyl)-nonanol, and in which the mixture also includes small amounts of other isomers listed in Table 4.

12. The alcohols of claim 1 characterized by substantial absence of alcohols with gem substituents and therefore substantially no quaternary carbon atom.

13. As a new compound, a $C_{14}$ alcohol suitable for use in formation of nonionic detergents and in liquid form, designated as 2-(3-methylbutyl)-5,6-dimethylheptanol.

14. As a new compound, a $C_{14}$ alcohol suitable for use in formation of nonionic detergents and in liquid form, designated as 2-(methylbutyl)5,6-dimethylheptanol.

15. As a new compound, a $C_{14}$ alcohol suitable for use in formation of nonionic detergents and in liquid form, designated as 2-(1-methylbutyl)-7-methyloctanol.

16. As a new compound, a $C_{14}$ alcohol suitable for use in formation of nonionic detergents and in liquid form, designated as 2-pentyl-5,6-dimethylheptanol.

17. As a new compound, a $C_{14}$ alcohol suitable for use in formation of nonionic detergents and in liquid form, designated as 2-(3-methylbutyl)-4-methyloctanol.

* * * * *